United States Patent [19]

Shawl

[11] Patent Number: 4,543,419

[45] Date of Patent: Sep. 24, 1985

[54] PROCESS FOR THE PREPARATION OF DIPHENYLMETHANE DICARBAMATES AND POLYMETHYLENE POLYPHENYL CARBAMATES

[75] Inventor: Edward T. Shawl, Wallingford, Pa.

[73] Assignee: Atlantic Richfield Company, Los Angeles, Calif.

[21] Appl. No.: 237,827

[22] Filed: Feb. 25, 1981

[51] Int. Cl.$^4$ .......................................... C07C 125/073
[52] U.S. Cl. ....................................................... 560/25
[58] Field of Search ............................................ 560/25

[56] References Cited

U.S. PATENT DOCUMENTS

| T994,004 | 5/1980 | Shawl | 560/25 |
| 3,277,098 | 10/1966 | Merten | 260/287 |
| 4,162,362 | 7/1979 | Shawl | 560/25 |

OTHER PUBLICATIONS

Braun, "Techniques of Polymer Synthesis and Characterization," pp. 197–202, 220–224 (1971).
Sokolov, "Synthesis of Polymers by Polycondensation," Daniel Davey & Co., pp. 27, 28, 34, 57–71 & 77–86 (1968).
Collins, "Experiments in Polymer Science," John Wiley & Sons, pp. 3–6 & 66 (1973).

*Primary Examiner*—Michael L. Shippen
*Attorney, Agent, or Firm*—Delbert E. McCaslin

[57] ABSTRACT

Diphenylmethane dicarbamates and polymethylene polyphenyl carbamate homologs and derivatives of these compounds are produced by the acid catalyzed condensation of an N-aryl carbamic acid ester, such as ethylphenylcarbamate, with a carbonyl compound, such as formaldehyde, at a reaction temperature of from about 30° C. to 170° C. while removing any water added with the reactants and the water of condensation formed in the reaction, by azeotropic distillation with an azeotroping solvent which is non-reactive with the reactants and products of the condensation and which form a binary minimum-boiling azeotrope with water within the condensation, temperature range at atmospheric, sub-atmospheric or super-atmospheric pressure.

9 Claims, No Drawings

PROCESS FOR THE PREPARATION OF DIPHENYLMETHANE DICARBAMATES AND POLYMETHYLENE POLYPHENYL CARBAMATES

FIELD OF THE INVENTION

The present invention relates to an improved process for the preparation of esters of aromatic carbamic acids (urethanes) particularly diphenylmethane dicarbamates and related higher homologs and derivatives by the acid catalyzed condensation of an N-aryl carbamic acid ester with a carbonyl compound selected from formaldehyde, paraformaldehyde or trioxane. Water added with the reactants and water formed by the condensation reaction are removed with an azeotroping solvent which forms a binary minimum-boiling azeotrope with water within the condensation temperature range at atmospheric, subatmospheric or or superatmospheric pressure.

BACKGROUND OF THE INVENTION

The polymeric aromatic carbamates (polyurethanes), such as the diphenylmethane dicarbamates and related higher homologs, the polymethylene polyphenyl carbamates, and especially the diethyl esters, are important products, particularly for use in the preparation of the commercially valuable diphenylmethane diisocyanates and mixtures of diisocyanates and polyisocyanates by the thermal decomposition of such polymeric aromatic carbamates in a suitable solvent as shown, for example, in Rosenthal et al, U.S. Pat. Nos. 3,962,302 and 3,919,279.

Prior art processes have been proposed for the preparation of polymeric aromatic carbamates (polyurethanes) by the acid condensation of N-aryl carbamic esters with carbonyl compounds such as formaldehyde, para-formaldehyde and a formaldehyde forming compound such as trioxane and ketones. Klauke et al, U.S. Pat. No. 2,946,768, describes the condensation of aryl carbamic esters with carbonyl compounds such as aldehydes and ketones with a dilute mineral acid. Shawl U.S. Pat. Nos. 4,162,362 and 4,202,986 disclose the condensation of N-aryl carbamic acid esters with formaldehyde, paraformaldehyde or trioxane in the presence of an organic sulfonic or halogenated organic sulfonic acid having an acid concentration of at least 75 percent and a Lewis acid intercalated in graphite respectively.

In processes employing dilute aqueous acid systems, the carbonyl compound such as formaldehyde tends to react at the nitrogen of the carbamate to produce along with some desired di- and polyurethanes, varying amounts, i.e., generally between 15 percent and 50 percent by weight of undesirable N-(alkoxycarbonyl)-phenylaminomethylphenyl compounds which include the di- and polyphenyl compounds, which compounds referred to as "N-benzyl" compounds are fully described in U.S. Pat. No. 4,146,727. Attempts to prepare diisocyanates and polyisocyanates or to otherwise use the mixture containing the polyurethanes and such amounts of the undesirable compounds, which compounds cannot be converted to isocyanates by pyrolysis, present many problems since there is no known method for separating the polyurethanes from the N-(alkoxycarbonyl)phenylaminomethylphenyl impurities. While U.S. Pat. No. 4,146,727 describes a method for converting the "N-benzyl" compounds employing certain strength acids it is advantageous to essentially avoid the formation of such impurities as will occur with dilute acid condensation systems or dilute acid condensation systems resulting from the water of condensation formed in the reaction.

Azeotropic distillation of water and azeotropic distillation during chemical processes are known. U.S. Pat. No. 3,000,859, describes the production of thermoplastics resins by the acid condensation of poly benzenoid aromatic hydrocarbons and aldehydes. U.S. Pat. No. 3,809,724 describes a process for the preparation and recovery of ethylene glycol by azeotropic distillation with a water-immiscible agent which forms a minimum-boiling azeotrope with the ethylene glycol.

SUMMARY OF THE INVENTION

This invention relates to an improved process for the preparation of a mixture of diphenylmethane dicarbamates and the higher molecular weight homologs, polymethylene polyphenyl carbamates, by the acid catalyzed condensation of an N-aryl carbamic acid ester with a carbonyl compound such as formaldehyde, paraformaldehyde or a formaldehyde forming compound such as trioxane, or mixtures thereof, at a temperature of from about 30° C. to 170° C. while removing water added with the reactants and water of condensation, by azeotroping off the water with an azeotroping solvent which is inert in the reaction at prevailing conditions and which forms a binary minimum-boiling azeotrope with water within the condensation temperature range at atmospheric, sub-atmospheric or superatmospheric pressures.

It is an object of the present invention to provide an improved process for the preparation of diphenylmethane dicarbamates and polymethylene polyphenyl carbamates in high yield by the acid condensation of an N-aryl carbamic acid ester with a carbonyl compound wherein the amount of acid catalyst needed to maintain an acid concentration of at least 75 percent during the reaction is substantially reduced.

It is another object of this invention to prevent an increase in the amount of water in the acid condensation of an N-aryl carbamic acid ester with formaldehyde or formaldehyde forming compounds, which water will dilute and weaken the acid strength of the system to below the desired 75 percent acid concentration thus allowing the inordinate production of N-benzyl compound impurities and lowering the direct yield of diphenylmethane dicarbamates and the related polymethylene polyphenyl carbamates.

These and other objects and advantages of this invention will become apparent from the description of the invention which follows and from the claims.

DESCRIPTION OF THE INVENTION

In accordance with the present invention an aromatic carbamic acid ester (N-arylcarbamic acid ester) such as, for example, a lower alkyl ester of phenyl carbamic acid, particularly ethylphenylcarbamate, is contacted with formaldehyde, para-formaldehyde or trioxane at a temperature of from about 30° C. to 170° C., under atmospheric, subatmospheric or superatmospheric pressure, in the presence of an acid catalyst to produce a reaction product mixture of diphenylmethane dicarbamates and polymethylene polyphenyl carbamates, while, during the condensation reaction , water added with the reactants and water of condensation is removed by azeotropic distillation with inert solvents.

The azeotroping solvents are inert in the reaction at reaction conditions and form a binary minimum-boiling azeotrope with water within the condensation reaction temperature range. By removing water as it is added or formed, the catalyst activity is maintained, i.e., the acid catalyst is kept at the desirable concentration of at least 75 percent to permit not only the use of smaller quantities of acid but higher yield of reaction product and a reduced production of undesirable "N-benzyl" compound impurities which result with a dilute acid catalyst system.

The acid catalyzed condensation reaction may be carried out in any suitable reactor which is generally equipped with a means for agitation, a means for regulating temperature and a means, such as a condenser, for removing the solvent-water azeotrope with preferably a means for returning the azeotroping solvent to the reactor, especially in a continuous operation. A general procedure for carrying out the reaction is to charge the N-aryl carbamic acid ester and a suitable azeotroping solvent into the reaction vessel together with the desired formaldehyde forming compound, and the desired acid catalyst, and then heat or maintain the mixture at the desired reaction temperature for the appropriate period while azeotroping off the water. The reaction may be carried out as a batch, semicontinuous or a continuous process and the order of addition of the materials may be varied to suit the particular apparatus employed. The reaction products are recovered and treated by any conventional method such as extraction of the acid medium with water or neutralization with an appropriate base and separation of the resulting phases, as well as distillation to remove solvent.

With respect to the present invention, the N-aryl carbamic acid esters employed as reactants in the acid catalyzed condensation reaction must contain one or more carbamic acid ester groups, i.e., —NHCOOR groups, wherein R is an alkyl group containing up to 8 carbon atoms, an aryl group or alkyl substituted aryl group having up to 4 carbon atoms in the alkyl substituent. The N-aryl group of the carbamic acid ester may also contain substituents such as alkyl, alkoxy, halogen, etc. on the ring. The lower alkyl esters, e.g., ethyl esters such as ethylphenylcarbamate are preferred. The N-aryl carbamic acid esters for use in the invention may be prepared for example by the process disclosed in Zajacek et al U.S. Pat. No. 3,895,054 wherein the carbamic acid esters (urethanes) are prepared by reacting an organic compound containing at least one hydroxyl group with carbon monoxide and a nitrogenous U organic compound at elevated temperature and pressure in the presence of a selenium catalyst and a base and/or water, or by any other known process for preparing aromatic carbamates.

The carbonyl compounds which may be employed in the process of the invention are formaldehyde and paraformaldehyde as well as trioxane which is capable of producing monomeric formaldehyde in the presence of acid. The quantity of the formaldehyde or formaldehyde forming compound employed in the reaction relative to the N-aryl carbamic acid ester employed is based on the degree of condensation or polymerization desired in the reaction product. Generally, the molar ratio of N-aryl carbamic acid ester to the carbonyl compound, in the form of free formaldehyde in the reaction mixture, will be in the range of about 1.5 to 8:1. At the high end of the range the production of dimeric carbamates will predominate whereas at the low end of the range the higher polymeric polymethylene polyphenyl carbamates will predominate.

The acid catalysts employed in the present invention are primarily those known and hereinbefore described. The acid catalysts include, for example, the mineral acids such as concentrated sulfuric acid, hydrochloric acid, phosphoric acid, etc., Lewis acids and Lewis acids intercalated in graphite such as tin(IV) chloride, boron trifluoride, iron(III) chloride, chromium chloride, palladium chloride, nickel chloride, cobalt chloride, aluminum trichloride and antimony pentafluoride, organic sulfonic and halogenated sulfonic acids such as methane, ethane, butane sulfonic acids, trifluoromethane sulfonic acid, trichloromethanesulfonic acid, p-toluene sulfonic acid, etc., as well as strongly acidic sulfonated aromatic ion exchange resins and perfluoroalkane sulfonic acid resins. The acid catalysts are generally employed in concentrations of from about 0.1 to 75 weight percent, preferably 5.0 to 50 weight percent, based on the N-aryl carbamate, which concentration within this range varies with the particular acid employed.

The azeotroping solvents which are stable and chemically inert to the components of the reaction system are generally employed, essentially in an anhydrous condition, in amounts of from about 10 to 90 weight percent, preferably 25 to 75 weight percent based on the total reaction mixture. The azeotroping solvents forming a binary minimum-boiling azeotrope with water within the condensation reaction temperature range of from about 30° C. to 170° C. at atmospheric, subatmospheric or superatmospheric pressure include, for example, nitrated and halogenated aromatic hydrocarbons having up to 10 carbon atoms such as nitrobenzenes, nitrotoluenes, chlorobenzene and bromobenzene, alkanes and substituted alkanes as well as cycloalkanes having up to 12 carbon atoms such as n-pentane, isopentane, n-hexane, n-heptane, nonane, 2-methylpentane, 3,4-dimethylhexane, 2-methylhexane, 3-ethylhexane, cyclohexane, methylcyclohexane, cyclopentane, ethylcyclohexane, cyclooctane, halogenated aliphatic compounds such as chloroform, carbon tetrachloride, dichloroethane, trichloroethane, tetrachloroethane, certain aliphatic carboxylic acids having up to 8 carbon atoms such as propionic and butyric and lower aliphatic alcohols (except methanol) having up to 8 carbon atoms such as ethanol, propanol, butanol, octanol, etc.

The reaction of the present invention including the azeotropic distillation will proceed at temperatures of from about 30° C. to 170° C. It is generally preferred to operate the process at temperatures of from 50° C. to 130° C. to obtain a convenient rate of condensation and maintain the water azeotrope. Operating temperature will of course be based on the azeotroping solvent and pressure employed in the reaction. The process may be carried out at atmospheric pressure. Subatmospheric pressure of from 15 mm Hg up to atmospheric may be used as well as superatmospheric pressures of up to 50 psig.

The following examples are provided to illustrate the invention in accordance with the principles of this invention, including examples of a comparative nature, but are not to be construed as limiting the invention in any way except as indicated by the appended claims.

Although the process of this invention will be directed primarily to the improved method for the preparation of diphenylmethane dicarbamate, ethyl esters and the polymethylene polyphenyl carbamates, ethyl esters by acid condensation of ethylphenylcarbamate and formaldehyde while removing water by azeotropic distillation, it is not intended that the process be limited to such ethyl ester compounds and those skilled in the art will recognize that the present invention is broadly applicable to the acid condensation reactions of other N-aryl carbamic acid esters as hereinabove described.

In the Examples which follow, the reactions except as otherwise noted, were run in a 300 ml or appropriate size three neck glass reaction flask fitted with a magnetic stirrer, a Dean Stark trap to collect water and athermometer. The reactants were charged to the reaction flask and the flask immersed into a constant temperature oil bath. At the end of the reaction time, water was added to the flask to quench the reaction and extract the acid catalyst medium. The condensate was washed with additional water or a 1 Normal solution of sodium hydroxide was added to neutralize any residual acid, and solvent if present, was removed by distillation. Conversion of the N-aryl carbamate charged and condensation product yield and polymer distribution were determined by high speed liquid chromatography.

EXAMPLE 1

A mixture of 30 g. ethylphenylcarbamate with 60 g. cyclohexane was combined with 1.90 g. paraformadehyde and 10.00 g. (85 weight percent) $H_2SO_4$ and refluxed for 30 minutes at 80° C. Water removed by azeotropic distillation with cyclohexane was collected in a Dean Stark apparatus; 2.2 g. of water was recovered. Analysis by liquid chromatography showed ethylphenylcarbamate conversion was 62 percent with 62 percent of the product as the (dimer) diphenylmethane dicarbamate, ethyl ester, 37 percent as higher molecular weight homologs and less than 1 percent as N-benzyl compound impurities.

EXAMPLE 2 (Comparative)

A mixture of 30 g. ethylphenylcarbamate with 1.90 g. paraformaldehyde and 10.00 g. sulfuric acid (85 weight percent) were mixed for 30 minutes at 80° C. with no provision for removing water formed in the reaction. Analysis showed ethylphenylcarbamate conversion was 62 percent with 62 percent of the production as diphenylmethane dicarbamate, ethyl ester, 27 percent as higher molecular weight homologs and 11 percent as N-benzyl compound impurities.

EXAMPLE 3 (Comparative)

Example 2 was repeated employing an additional 10 g. of concentrated (96 weight percent) sulfuric acid added during the condensation reaction to maintain an acid concentration of approximately 85 percent for the 30 minute reaction period. Analysis of the reaction product showed an ethylphenylcarbamate conversion of 62 percent with 66 percent of the product as diphenylmethane dicarbamate, ethyl ester, 32 percent as higher molecular weight homologs and 2 percent as N-benzyl compound impurities. These results indicated that in the absence of water removal at least as much as 100 percent additional acid was required to obtain a satisfactory reaction product.

EXAMPLE 4

A mixture of 30 g. ethylphenylcarbamate with 60 g. nitrobenzene and 20 g. n-heptane was combined with 1.90 g. trioxane and 20.0 g. 85 percent phosphoric acid. The mixture was refluxed for 60 minute at 98° C., during which time water was removed by azeotropic distillation. 4.0 g. water was recovered compared to 4.1 g. theoretical value based on water in the phosphoric acid and water formed in the condensation reaction. Analysis showed an ethylphenylcarbamate conversion of 61 percent with 55 percent of the product as dimer, 43 percent as higher molecular weight homologs and about 2 percent as N-benzyl compound impurities.

EXAMPLE 5

Example 4 was repeated using 30 g. ethylphenylcarbamate, 60 g. n-octane, 1.90 g. trioxane and 20.0 g. 85 percent phosphoric acid. The mixture was refluxed for 105 minutes at 116° C. Ethylphenylcarbamate conversion was 65 percent with 58 percent of the product as dimers 42 percent as higher molecular weight homologs and no N-benzyl compound impurities.

EXAMPLE 6 (Comparative)

30 g. ethylphenylcarbamate, 30 g. nitrobenzene, 1.90 g. paraformaldehyde, and 30 g. 85 percent phosphoric acid were heated for 2 hours at 120° C. with no provision for water removal. Ethylphenylcarbamate conversion was 57 percent with 64 percent of the product as dimers, 12 percent as higher molecular weight homologs and 24 percent as N-benzyl compound impurities.

EXAMPLE 7

30 g. ethylphenylcarbamate, 30 g. carbon tetrachloride, 1.90 g. paraformaldehyde and 10.0 g. concentrated sulfuric (96 weight percent) acid were refluxed for 30 minutes at 80° C. with water taken overhead by azeotropic distillation. Ethylphenylcarbamate conversion was 63 percent with 66 percent of the product as dimers, 33 percent of higher molecular weight homologs and less than 1 percent as N-benzyl compound impurities.

EXAMPLE 8

A continuous reactor was set up with provision for separately feeding a solution of ethylphenylcarbamate in nitrobenzene, a methane sulfonic acid catalyst and an aqueous formaldehyde solution. The reactor was operated at 15 mm Hg with the reaction temperature held at 75° C. Water was removed from the system by azeotropic distillation with the nitrobenzene. Product flowed from this condensation reactor to a separate rearrangement reactor operated at atmospheric pressure wherein it was held in the presence of methane sulfonic acid to convert N-benzyl compounds to carbamates according to the process described in U.S. Pat. No. 4,146,727.

In a typical run, a 50 weight percent solution of ethylphenylcarbamate in nitrobenzene was used along with 50 percent aqueous formaldehyde, and 99 weight percent methane sulfonic acid as the catalyst. The feed ratios were 100:7.6:35 percent by weight for ethylphenyl-carbamate solution:formaldehyde solution:acid catalyst. Residence time was 15 minutes in the condensation reactor at 75° C. and 50 minutes in the rearrangement reactor at 80° C. Rates of removal of water was adjusted so that about 65 percent of the water in the system was taken overhead. Ethylphenylcarbamate conversion was 65 percent with 58 percent of product as dimers, 41+ percent of higher molecular weight homologs and less than 1 percent as N-benzyl compound impurities.

EXAMPLE 9

34 g. butylphenylcarbamate, 90 g. n-hexane, 10.10 g. 30 percent aqueous formaldehyde and 23 g. of methane sulfonic acid were heated at 15 psig with a 95° C. bath for 90 minutes and provision to remove water by azeotropic distillation. Analysis showed the butylphenylcarbamate conversion was 90 percent with 43 percent of the product as dimer, 56+ percent as higher molecular weight homologs and less than 1 percent as N-benzyl compounds.

EXAMPLE 10

30 g. ethylphenylcarbamate, 90 g. chloroform, 10.10 g. 30 percent aqueous formaldehyde and 23 g. of methane sulfonic acid were heated at 40 psig with a 100° C. bath for 90 minutes. Water was removed during the reaction by azeotropic distillation. Ethylphenylcarbamate conversion was 92 percent with 40 percent of the product as dimer, 59+ percent higher molecular weight homologs and less than 1 percent N-benzyl compounds.

We claim:

1. In a process for the preparation of a mixture of diphenylmethane dicarbamates and polymethylene polyphenyl carbamates by the acid catalyzed condensation of an N-aryl carbamic acid ester with formaldehyde, para-formaldehyde or trioxane or mixtures thereof, at temperatures of from about 30° C. to 170° C., the improvement which comprises removing from the reaction zone with water collection means, during said condensation, water added with reactants and water of condensation by azeotropic distillation with an inert water-azeotroping solvent which forms a binary minimum-boiling azeotrope with water within the condensation temperature range at atmospheric, sub-atmospheric or super-atmospheric pressure, in order to maintain an acid concentration of at least 75 weight percent during the reaction and reduce production of N-(alkoxycarbonyl)phenylaminomethylphenyl impurities.

2. A process according to claim 1 wherein the azeotroping solvent is selected from the group consisting of nitrated and halogenated aromatic hydrocarbons having up to 10 carbon atoms, alkanes, substituted alkanes and cycloalkanes having up to 12 carbon atoms, lower aliphatic alcohols having up to 8 carbons atoms, aliphatic carboxylic acids having up to 8 carbon atoms and halogenated aliphatic compounds.

3. A process according to claim 2 wherein the azeotroping solvent is cyclohexane, n-heptane, n-octane, nitrobenzene, carbon tetrachloride, n-hexane, or chloroform.

4. A process according to claim 3 wherein the azeotroping solvent is nitrobenzene.

5. A process according to claim 1 wherein the azeotroping solvent is employed in an amount of from about 10 to 90 weight percent based on the total reaction mixture.

6. A process according to claim 1 wherein the reaction temperature is from 50° C. to 130° C.

7. A process according to claim 1 wherein the process is carried out at a sub-atmospheric pressure of between about 15 mm Hg and atmospheric pressure.

8. A process according to claim 1 wherein the process is carried out at a super-atmospheric pressure of between atmospheric pressure and 50 psig.

9. In a process for the preparation of a mixture of diphenylmethane dicarbamate, diethyl ester and polymethylene polyphenyl carbamates, ethyl esters, by the acid catalyzed condensation of ethylphenylcarbamate with formaldehyde at a temperature of from about 50° C. to 130° C., the improvement which comprises removing from the reaction zone with water collection means, during said condensation by azeotropic distillation with from 25 to 75 weight per cent, based on the total reaction mixture, of an inert water-azeotropic solvent which forms a binary minimum-boiling azeotropic with water within the temperature range of from 50° C. to 130° C. at atmospheric, sub-atmospheric or superatmospheric pressure, in order to maintain an acid concentration of at least 75 weight percent during the reaction and reduce production of N-[(ethoxycarbonyl)phenylaminomethyl]phenyl carbamate acid, ethyl ester impurities.

* * * * *